United States Patent [19]

Salkin

[11] 4,235,884

[45] Nov. 25, 1980

[54] METHOD FOR THE PREPARATION OF STABLE AQUEOUS SOLUTIONS OF COMPLEXES OF POLYVINYLPYRROLIDONE AND OF HALOGENS AND THE SOLUTIONS OBTAINED THEREBY

[76] Inventor: Nicolas Salkin, 36 Avenue de Villepreux, Vaucresson - (Hauts-de-Seine), France

[21] Appl. No.: 17,197

[22] Filed: Mar. 5, 1979

[30] Foreign Application Priority Data

Mar. 17, 1978 [FR] France ............................ 78 07797

[51] Int. Cl.³ .................... A61K 31/79; A61K 33/18; C07D 207/444
[52] U.S. Cl. ............................. 424/150; 260/326.25
[58] Field of Search ..................... 424/50; 260/326.25

[56] References Cited

U.S. PATENT DOCUMENTS

| | | | |
|---|---|---|---|
| 2,706,701 | 4/1955 | Beller et al. | 424/150 |
| 2,739,922 | 3/1956 | Shelanski | 424/150 |
| 2,826,532 | 3/1958 | Hosmer | 424/150 |
| 2,900,305 | 8/1959 | Siggia | 424/150 |

*Primary Examiner*—Jose Tovar

[57] ABSTRACT

The invention relates to the chemical industry.

A stable aqueous solution of a complex of polyvinylpyrrolidone and halogen is prepared by carrying out the following steps:
  (a) The halogen is put in solution in the presence of PVP in a solvent that solubilizes the two components, the said solvent having a boiling point lower than that of water, being insoluble in water, and forming no azeotrope with the latter;
  (b) The solution obtained is heated to react the PVP and the halogen;
  (c) The said solvent is displaced by addition of water brought to a temperature higher than the boiling point of the said solvent.

These solutions are used as germicides and bactericides.

3 Claims, No Drawings

METHOD FOR THE PREPARATION OF STABLE AQUEOUS SOLUTIONS OF COMPLEXES OF POLYVINYLPYRROLIDONE AND OF HALOGENS AND THE SOLUTIONS OBTAINED THEREBY

The present invention relates to a method of preparation of stable aqueous solutions of complexes of polyvinylpyrrolidone and halogens, and in particular of complexes of polyvinylpyrrolidone (a polymer of vinyl-1 pyrrolidone-2) and iodine.

Many patents are known which have described the use and the manufacture of halogenated polyvinylpyrrolidone (PVP-X), and in particular, of iodized polyvinylpyrrolidone (PVP-I).

The complex of PVP-I was sought after primarily for its antiseptic properties, its non-toxicity, and its very low vapor tension when in aqueous solution. Its solutions in water and therefore odorless, and non-irritating, and can be used as pre-operatory disinfectants directly on the skin of the patient operated on, or as a disinfectant soap for the hands of surgeons and nurses because they are easy to rinse off and do not stain drapes and natural fibers.

PVP-I is described as being "a chemical compound in which iodine is coupled with an inert vehicle that slowly releases the active iodine. This combination causes the toxic and irritant power of free iodine to disappear. It also enhances the stability of the antiseptic, avoiding the transformation in storage of the iodine into an inactive triodized derivative" (Journal de Medecine de Caen 9,no. 2, pages 111 to 116).

The PVP-I most widely used is the one containing 17% of iodine bi-sublimate, 83% PVP of molecular weight 40,000, with a given percentage of moisture, and containing about 10% free iodine titerable by sodium thiosulphate.

Attempts have also been made to obtain PVP-bromine-I and PVP-chlorine-I complexes for use as bleaching agents, antiseptics, germicides and bactericides.

All known patents and techniques describing the preparation of PVP-X mention the dry mixing of PVP, anhydrous or slightly hydrated with halogen, then raising the temperature (90° to 100° C.). Another description of the preparation of a complex of PVP and iodine involves mixing a solution of PVP in a solvent such as methanol, ethanol and methylene chloride with a solution of iodine in a similar solvent. But a solution of PVP and iodine in methylene chloride cannot be used as is since the solvent is toxic and malodorous. There is also mention of the preparation of a solution of PVP-I in water with addition of an aqueous solution of PVP in an aqueous solution of iodine such as a Lugol solution (iodine: 1 g, potassium iodide: 10 g, distilled water qsp: 100), then mixing. The result is an aqueous solution of PVP-I containing variable proportions of free iodine, iodide ion and bound iodine.

It was determined long ago that the ratio of free iodine to iodide ion should be equal to 2 to 1 for a stable aqueous solution of PVP-I. In the case of a solution of PVP and iodine prepared by addition of an aqueous solution of PVP to a Lugol solution, the result is not a solution in which there is a soluble complex of PVP-I, since the iodine has already been solubilized by the potassium iodide.

Attempts have therefore been made to modify the preparation of the complex/in such a way as to obtain aqueous solutions which are stable as to pH and the ratio of the quantity of free iodine to the quantity of iodide ion.

In general, the preparation of stable aqueous solutions of these complexes according to prior art, consists in preparing an anhydrous complex by adding, perhaps, a stabilizing product (for example sodium bicarbonate or a sodium or potassium iodide) during the mixing of the halogen with the polymer. Then the complex PVP-X is put into solution.

Consequently, one object of the present invention is to obtain stable aqueous solutions of halogenated PVP by a method that is economical and easy to apply.

It was found, surprisingly, that by putting the halogen and the PVP into solution in the same solvent, then, after heating the solution, displacing the solvent with hot water, a stable solution of the PVP-X complex is obtained directly. The halogen can be used as is, or in the form of an alkaline, or alkaline-earth compound.

According to the invention, the halogen is put in solution in an organic solvent of the halogen, which is also a solvent of the PVP, this solvent having a low boiling point (less than 100° C.), being almost insoluble in water, and forming no azeotrope with the latter. Then the resulting solution is heated to react the halogen and polyvinylpyrrolidone to form the complex. The solvent is then displaced by adding hot water, i.e. having a temperature higher than the boiling point of the solvent.

Among such organic solvents, the following can be distinguished in particular:

| | |
|---|---|
| Methylene chloride | boiling point 40–41° C. |
| Ethyl chloride | boiling point 12.3° C. |
| Chloroform | boiling point 61–62° C. |
| Acetone | boiling point 56.5° C. |

The alcohols, ethanol and methanol, which are powerful solvents of the two components, PVP and iodine, cannot be used because they are very soluble in water and hence are not displaced by the latter. Moreover, they are very hygroscopic and form azeotropes with water. Sulfide of carbon (boiling point 46.5° C.) is explosive, dangerous, and forms an azeotrope with water at 42.6° C. PVP is not soluble either in ether or in benzene. Acetone is a very dangerous solvent, as is ethyl chloride which is flammable and explosive chloroform is toxic. Methylene chloride is a powerful solvent of PVP and iodine is insoluble in water.

Furthermore, methylene chloride boils at a very low temperature (40°–41° C.), close to the temperature of sublimation of iodine. It is non-flammable, almost insoluble in water, whence it can easily be extracted, either by vacuum or by raising the temperature. Its price is low and storage for recycling presents no difficulties. In addition, it has a very characteristic odor which makes it easy to detect traces that have not been eliminated.

If the final distillation is not complete it is detectable, even in an infinitesimal quantity. A mixture of solvents with low boiling point can be used.

The following description, with reference to the examples indicated with no limiting character, will make it possible to understand how the invention may be applied in practice.

EXAMPLE 1

Dissolve cold, 300 g of PVP and 60 g of iodine in 600 g of methylene chloride.

Heat for 8 hours at 60°–65° C. in a closed vessel. Cool to 40°–42° C. and introduce deionized water (pH neutral) at 42°–44° C., opening the distillation valves through which the methylene chloride escapes. It is cooled and recovered. Add a total of 1,640 ml of water to obtain, after elimination of the methylene chloride, 2 liters of solution titering 1.87% free iodine. To drive off the last traces of methylene chloride, it is possible either to pour the last traces of methylene chloride, it is possible either to pour the last 250 ml of water at 80°–85° C., or place the vessel in a vacuum. The PVP-iodine complex has a vapor tension so low that little iodine escapes, even when the temperature is raised. This, moreover is of no importance because the iodine is recovered in the subsequent production, thanks to the recycling of the solvent.

The aqueous solution of the complex has a ratio of free iodine to complexed iodine of 66 to 34 (about 2 to 1). Its pH is comprised between 1 and 2. Furthermore, the ratio of total iodine to free iodine is about 3 to 2, the ratio of PVP of total iodine is about 5 to 1.

EXAMPLE 2

Dissolve, cold, 150 g of PVP and 30 g of iodine in 600 g of methylene chloride.

Leave under agitation overnight and in the morning, heat to 60°–65° C. for 4 and one half hours. Begin to pour hot water (42°–44° C.) (657 ml) and distill the methylene chloride which departs almost instantaneously. Obtain 837 g of a solution titering 2.37% free iodine, with a pH comprised between 1 and 2.

EXAMPLE 3

Dissolve cold, 400 g of PVP and 80 g of iodine in 750 g of methylene chloride.

Heat for 9 hours at 60°–65° C., lower the temperature to 45° C., begin to pour the hot water (42°–44° C.) (1,328 ml), open the distillation valves and, when all the methylene chloride seems to have been eliminated, place the apparatus in a vacuum to eliminate the last traces of methylene chloride. Obtain 1,808 g of solution titering 3.01% free iodine and very acid pH.

The solutions obtained are very effective against micro-organisms causing disease in man, animals and plants. They have the fast action and the very wide spectrum of iodine against bacteria, viruses, fungi, spores, protozoa and molds. They can be effective against certain insects and nematodes.

It is, of course, possible to prepare aqueous solutions of a PVP-iodine complex with a ratio of total iodine to free iodine different from 3 to 2, and whose ratio of PVP to total iodine is different from 5 to 1, only the ratio of free iodine to iodide must remain equal to 2 to 1 for the product to be stable. It is possible to provide iodized PVP's with more or less PVP, and with PVP's of lower or higher molecular weight, hence more or less viscous and more or less soluble.

I claim:

1. Method for preparation of a stable aqueous solution of a complex of halogen and polyvinylpyrrolidone (PVP) comprising the following steps:
    (a) halogen selected from the group consisting of chlorine, iodine and bromide is put in solution in the presence of PVP in a solvent which solubilizes the two components, the said solvent having a boiling point lower than that of water, being insoluble in water, and forming no azeotrope with the latter;
    (b) The solution obtained is heated to react the PVP and the halogen;
    (c) The said solvent is displaced by addition of water brought to a temperature higher than the boiling point of the said solvent.

2. Method according to claim 1 in which the solvent is chosen from the group formed by methylene chloride and chloroform.

3. Method according to claim 1 in which the halogen is iodine, the solvent is methylene chloride, the solution of PVP and iodine is heated in a closed vessel to a temperature comprised between 60° and 65° C., the said solution is cooled to a temperature comprised between 40° and 42° C., and the methylene chloride is displaced by addition of water at a temperature of 42°–44° C.

* * * * *